United States Patent
Jonishi et al.

(10) Patent No.: US 9,580,401 B2
(45) Date of Patent: Feb. 28, 2017

(54) METHOD FOR PRODUCING A SUBSTITUTED BENZOIC ACID COMPOUND

(71) Applicant: ISHIHARA SANGYO KAISHA, LTD., Osaka (JP)

(72) Inventors: Hisayoshi Jonishi, Shiga (JP); Tomohiro Okamoto, Shiga (JP); Norio Adachi, Shiga (JP); Akihiko Isogai, Shiga (JP); Tatsuya Jukurogi, Shiga (JP); Hideaki Konishi, Shiga (JP); Fumihiro Fukui, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 7 days.

(21) Appl. No.: 14/398,246

(22) PCT Filed: Apr. 30, 2013

(86) PCT No.: PCT/JP2013/062646
§ 371 (c)(1),
(2) Date: Oct. 31, 2014

(87) PCT Pub. No.: WO2013/168642
PCT Pub. Date: Nov. 14, 2013

(65) Prior Publication Data
US 2015/0119586 A1   Apr. 30, 2015

(30) Foreign Application Priority Data
May 8, 2012  (JP) .................. 2012-107065

(51) Int. Cl.
*C07D 319/06* (2006.01)
*C07D 317/22* (2006.01)
(Continued)

(52) U.S. Cl.
CPC .......... *C07D 319/06* (2013.01); *C07C 317/22* (2013.01); *C07D 317/22* (2013.01); *C07D 317/26* (2013.01)

(58) Field of Classification Search
CPC .................................................. C07D 319/06
See application file for complete search history.

(56) References Cited

U.S. PATENT DOCUMENTS 4,638,067 A   1/1987   Culbertson et al.
4,665,079 A   5/1987   Culbertson et al.
(Continued)

FOREIGN PATENT DOCUMENTS

CN   1179778   4/1998
CN   1509285   6/2004
(Continued)

OTHER PUBLICATIONS

Gu, X., et al. "Design, Synthesis, and Monoamine Transporter Binding Site Affinities of Methoxy Derivatives of Indatraline." J. Med. Chem. (2000), vol. 43, pp. 4868-4876.*

(Continued)

*Primary Examiner* — Noble Jarrell
*Assistant Examiner* — John S Kenyon
(74) *Attorney, Agent, or Firm* — Greenblum & Bernstein, P.L.C.

(57) ABSTRACT

To provide an industrial method for producing a substituted benzoic acid compound useful as an intermediate of pharmaceutical and agricultural chemicals with high purity and high yield.

A compound represented by the formula (II):

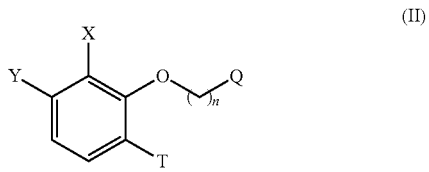

(wherein Q is a 5- or 6-membered saturated heterocyclic group (the heterocyclic group may be substituted by alkyl) containing one or two of at least one type of hetero atom selected from the group consisting of an oxygen atom and a sulfur atom, or dialkoxymethyl, T is trifluoromethyl, nitro, cyano, —SOA$^1$, —SO$_2$A$^1$, —PO(OA$^1$)(OA$^2$), —COA$^1$, —CO$_2$A$^1$ or —CONA$^1$A$^2$, each of A$^1$ and A$^2$ which are independent of each other, is a hydrogen atom, alkyl or haloalkyl, X is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, di(haloalkyl)aminosulfonyl, nitro or cyano, Y is a chlorine atom, a bromine atom or an iodine atom, and n is an integer of from 1 to 6), carbon monoxide and a compound represented by the formula R—OH (wherein R is alkyl) are reacted, followed by hydrolysis to obtain a compound represented by the formula (I):

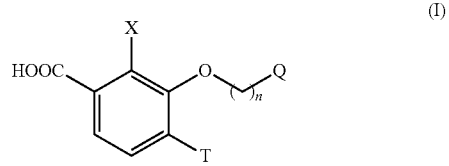

wherein Q, T, X and n are as defined above.

8 Claims, No Drawings

(51) Int. Cl.
*C07C 317/22* (2006.01)
*C07D 317/26* (2006.01)

(56) References Cited

U.S. PATENT DOCUMENTS

| | | |
|---|---|---|
| 4,771,054 A | 9/1988 | Domagala et al. |
| 4,777,175 A | 10/1988 | Culbertson et al. |
| 4,895,944 A | 1/1990 | Hayakawa et al. |
| 5,281,612 A | 1/1994 | Domagala et al. |
| 6,004,903 A | 12/1999 | von Deyn et al. |
| 6,153,759 A | 11/2000 | von Deyn et al. |
| 2003/0153465 A1 | 8/2003 | Schallner et al. |
| 2005/0009704 A1 | 1/2005 | Schallner et al. |

FOREIGN PATENT DOCUMENTS

| | | | |
|---|---|---|---|
| EP | 2103215 | 9/2009 | |
| JP | 54-145633 | 11/1979 | |
| JP | 60-188349 | 9/1985 | |
| JP | S60-214773 | 10/1985 | |
| JP | S63-264468 | 11/1988 | |
| JP | 2006-16389 | 1/2006 | |
| WO | 96/26200 | 8/1996 | |
| WO | 01/53275 | 7/2001 | |
| WO | WO 0172960 A2 * | 10/2001 | ........... C07C 311/47 |
| WO | WO 2006076706 A1 * | 7/2006 | ........... C07D 213/56 |
| WO | WO 2007082098 A2 * | 7/2007 | ........... A01N 43/40 |
| WO | WO 2009049098 A2 * | 4/2009 | ........... C07D 403/04 |

OTHER PUBLICATIONS

Minutolo, F., et al. "Diaryl-substituted salicyl- and anthranyl-ketoximes as potential estrogen receptor ligands." IL FARMACO. (2004), vol. 59, pp. 601-607.*
Jin, Q., et al. "Discovery of potent and orally bioavailable N,N'-diarylurea antagonists for the CXCR2 chemokine receptor." Bioorganic & Medicinal Chemistry Letters. (2004), vol. 14, pp. 4375-4378.*
Grivani, G., et al. "A new oxidovanadium(IV) complex containing an O, N-bidentate Schiff base ligand: Synthesis, characterization, crystal structure determination, thermal study and catalytic activity for an oxidative bromination reaction." Polyhedron. (2014), vol. 68, pp. 144-150.*
American Chemical Society. STN Database. RN 83577-91-7.*
American Chemical Society. STN Database. RN 73289-60-8.*
American Chemical Society. STN Database. RN 1476043-16-9.*
Search report (English and Japanese) from International Patent Application. No. PCT/JP2013/062646, dated Aug. 13, 2013.
International Preliminary Report (English) on Patentability form application No. PCT/JP2013/062646, dated Nov. 20, 2014.
Chinese Office Action with English Translation in respect to Chinese Application No. 201380023855.X, mailed Jul. 1, 2015.
Extended European Search Report in respect to European Application No. 13788182.7, dated Nov. 5, 2015.

* cited by examiner

METHOD FOR PRODUCING A SUBSTITUTED BENZOIC ACID COMPOUND

TECHNICAL FIELD

The present invention relates to a method for producing a substituted benzoic acid compound useful as an intermediate for production of pharmaceutical and agricultural chemicals.

BACKGROUND ART

Patent Document 1 discloses a method for producing a substituted benzoic acid from 2,4-substituted hydroxybenzoic acid ester as a starting material. This production method has problems such that methyl dichlorobenzoate as a starting material is hardly prepared and is industrially hardly available, anhydrous sodium thiomethoxide used for alkylthiolation of the starting material is industrially hardly available, and the selectivity of the alkylthiolation is low and the yield is low.

PRIOR ART DOCUMENTS

Patent Documents

Patent Document 1: JP-A-2006-16389

DISCLOSURE OF INVENTION

Technical Problem

The object of the present invention is to provide a method for industrially producing a substituted benzoic acid compound with high purity and high yield.

Solution to Problem

The present inventors have conducted extensive studies to achieve the above object and as a result, they have found a method for industrially producing, with high purity and high yield, a compound represented by the formula (I):

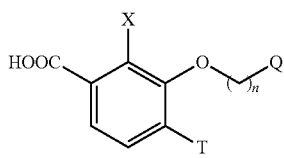

(I)

wherein Q is a 5- or 6-membered saturated heterocyclic group (the heterocyclic group may be substituted by alkyl) containing one or two of at least one type of hetero atom selected from the group consisting of an oxygen atom and a sulfur atom, or dialkoxymethyl;
T is trifluoromethyl, nitro, cyano, —$SOA^1$, —$SO_2A^1$, —$PO(OA^1)(OA^2)$, —$COA^1$, —$CO_2A^1$ or —$CONA^1A^2$, and each of $A^1$ and $A^2$ which are independent of each other, is a hydrogen atom, alkyl or haloalkyl;
X is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, di(haloalkyl)aminosulfonyl, nitro or cyano; and
n is an integer of from 1 to 6, which comprises reacting a compound represented by the formula (II):

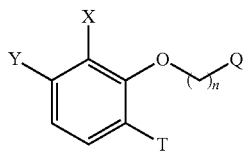

(II)

wherein Y is a chlorine atom, a bromine atom or an iodine atom; and
Q, T, X and n are as defined above,
carbon monoxide and a compound represented by the formula R—OH (wherein R is alkyl) to produce a compound represented by the formula (III):

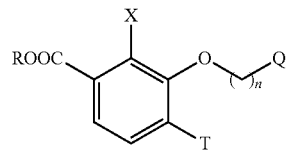

(III)

wherein Q, R, T, X and n are as defined above,
and hydrolyzing the compound represented by the formula (III).

That is, the present invention is characterized in that a compound represented by the above formula (II), carbon monoxide and a compound represented by the formula R—OH (wherein R is alkyl) are reacted to produce a compound represented by the above formula (III), and the compound of the formula (III) is hydrolyzed to produce a compound represented by the above formula (I).

Further, the present invention provides a compound represented by the above formula (II) useful for production of the compound represented by the above formula (I) and its production method.

Advantageous Effects of Invention

According to the production method of the present invention, a compound represented by the above formula (I) can be produced industrially with high purity and high yield, and the obtained substituted benzoic acid is preferably used as an intermediate for production of pharmaceutical and agricultural chemicals.

DESCRIPTION OF EMBODIMENTS

In this specification, e.g. "a compound represented by the formula (I)" may sometimes be abbreviated as "a compound of the formula (I)". The same applies to the other compounds.

Now, substituents (for example, Q, T and X) in the formulae (I), (II), (III) and the like will be described.

As Q, the 5- or 6-membered saturated heterocyclic group containing one or two of at least one type of hetero atom selected from the group consisting of an oxygen atom and a sulfur atom may, for example, be tetrahydrofuran-2-yl, tetrahydrofuran-3-yl, dioxolan-2-yl, dioxolan-4-yl, tetrahydropyran-2-yl, 1,4-dioxan-2-yl, 1,3-dioxan-2-yl, 1,3-dioxan-4-yl, tetrahydrothiophen-2-yl, tetrahydrothiopyran-2-yl, 1,3-dithian-2-yl, 1,4-dithian-2-yl, 1,4-thioxan-2-yl or 1,4-thioxan-3-yl.

Further, the heterocyclic group may be substituted by alkyl. The alkyl have from 1 to 6 carbon atoms, preferably one or two carbon atoms, and may be either linear or branched.

In each of Q, T, X and R, the alkyl or alkyl moiety may be a 1-6 linear or branched alkyl, such as methyl, ethyl, propyl, isopropyl, butyl, tert-butyl, pentyl or hexyl. Among them, preferred is methyl or ethyl.

The halogen in each of T and X or the halogen as a substituent may be a fluorine, chlorine, bromine or iodine atom, and preferred is a fluorine atom or a chlorine atom. The number of halogen as a substituent may be one or more, and in the case of two or more, the respective halogen atoms may be the same or different. Further, the position of substitution by halogen may be any position.

The compound of the above formula (I) may be produced by the following reaction [A]:

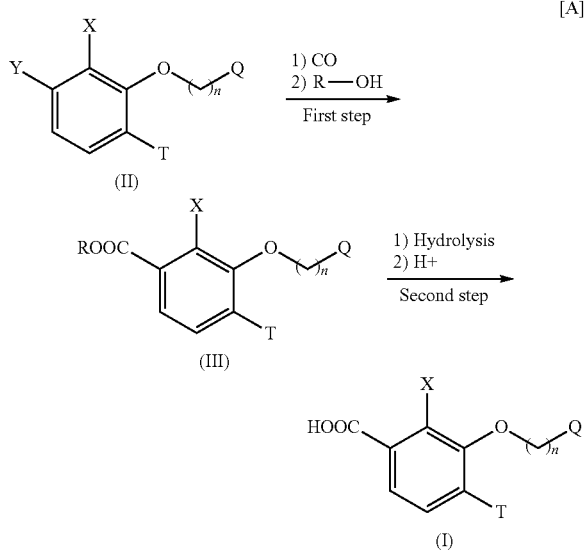

In the above formula, Q, T, X, Y, n and R are as defined above.

In the reaction [A], carbon monoxide may be used in an amount of usually from 1 to 10 equivalent amount, preferably from 1 to 4 equivalent amount per 1 mol of the compound of the formula (II). Further, the pressure may be usually from 0.1 to 10 MPa, preferably from 0.5 to 5 MPa. However, depending upon the reaction conditions, an amount or a pressure out of such a range may be employed.

In the reaction [A], the compound represented by the formula R—OH may be used in an amount of at least 1 equivalent amount per 1 mol of the compound of the formula (II). Further, if it is used in an excessive amount, it may also function as a solvent. Its amount is preferably from 1 to 30 equivalent amount per 1 mol of the compound of the formula (II).

However, depending upon the reaction conditions, an amount out of such a range may be used.

In R—OH, R may be a 01-6 alkyl such as methyl, ethyl, propyl, isopropyl, butyl, tert-butyl, pentyl or hexyl, and preferred is methyl.

In the reaction [A], the first step may be carried out usually in the presence of a base and a transition metal catalyst.

The base may, for example, be an alkali metal hydroxide such as sodium hydroxide or potassium hydroxide; an alkaline earth metal hydroxide such as calcium hydroxide or magnesium hydroxide; an alkali metal carbonate such as sodium carbonate or potassium carbonate; an alkaline earth metal bicarbonate such as calcium bicarbonate or magnesium bicarbonate; an alkali metal bicarbonate such as sodium bicarbonate or potassium bicarbonate; an alkali metal carboxylate such as sodium acetate or potassium acetate; an alkaline earth metal carboxylate such as calcium acetate or magnesium acetate; or a tertiary amine such as trimethylamine, triethylamine, diisopropylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene or 1,4-diazabicyclo[2.2.2]octane. Among them, preferred is an alkali metal carbonate, an alkali metal bicarbonate, an alkali metal carboxylate, triethylamine or the like. Still further, among them, preferred is an alkali metal carbonate or triethylamine with a view to further improving the yield. The alkali metal carbonate is preferably sodium carbonate or potassium carbonate. Such bases may be used alone or in combination of two or more.

The base may be used in an amount of usually from 1 to 5 equivalent amount, preferably from 1 to 3 equivalent amount per 1 mol of the compound of the formula (II). However, depending upon the reaction conditions, an amount out of such a range may be used.

The transition metal catalyst may be a complex of palladium, rhodium, ruthenium, nickel, cobalt, molybdenum or the like. In this reaction, a complex containing palladium is particularly useful. The catalyst containing palladium may be known one used for carbonylation of an organic halide. It may, for example, be palladium on carbon, palladium chloride, palladium acetate, dichlorobis(acetonitrile)palladium, dichlorobis(benzonitrile)palladium, bis(dibenzylideneacetone)palladium or bis(acetylacetonato)palladium.

Further, the catalyst containing palladium may, for example, be also dichlorobis(triphenylphosphine)palladium, dichlorobis(triisopropylphosphine)palladium, tetrakis(triphenylphosphine)palladium, dichloro(1,4-bis(diphenylphosphino)butane)palladium or dichlorobis(triphenylphosphite) palladium, each containing phosphine as a ligand.

Further, a palladium complex containing no tertiary phosphine or tertiary phosphite as a ligand may be reacted with a tertiary phosphine or a tertiary phosphite in the reaction system to form a palladium complex containing the tertiary phosphine or tertiary phosphite as a ligand, which is used as a catalyst as it is. The tertiary phosphine or the tertiary phosphite may, for example, be triphenylphosphine, phenyldimethylphosphine, tri-o-tolylphosphine, tri-p-tolylphosphine, 1,2-bis(diphenylphosphino)ethane, 1,3-bis(diphenylphosphino)propane, 1,4-bis(diphenylphosphino)butane or triphenylphosphite. Among them, use of a palladium complex containing a tertiary phosphine as a ligand as the transition metal catalyst is preferred with a view to further improving the yield. As such a transition metal catalyst, a catalyst having a tertiary phosphine preliminarily coordinated to palladium may be used, or a palladium complex containing no tertiary phosphine as a ligand may be reacted with a tertiary phosphine in the reaction system, and the resulting complex may be used as a catalyst. Such a tertiary phosphine is preferably 1,2-bis(diphenylphosphino)ethane, 1,3-bis(diphenylphosphino)propane or 1,4-bis(diphenylphosphino)butane.

The catalyst containing palladium may be used in an amount of usually from 0.001 to 0.5 equivalent amount, preferably from 0.001 to 0.1 equivalent amount per 1 mol of the compound of the formula (II). Further, in a case where a palladium complex containing a tertiary phosphine or a tertiary phosphite as a ligand is formed in the reaction system and used as a catalyst as it is, the ligand may be used in an amount of usually from 1 to 50 equivalent amount, preferably from 1 to 10 equivalent amount to the palladium atom in the complex containing no tertiary phosphine or tertiary phosphite as a ligand. However, depending upon the reaction conditions, an amount out of such a range may be used.

In the reaction [A], the first step may be carried out in the presence of a solvent as a case requires.

The solvent is not particularly limited so long as it is inert to the reaction and may, for example, be an alcohol such methanol, ethanol, propanol, n-butanol or tert-butanol; an aliphatic hydrocarbon such as pentane, hexane, heptane, octane or cyclohexane; an aromatic hydrocarbon such as benzene, toluene or xylene; a halogenated hydrocarbon such as chlorobenzene, dichlorobenzene, dichloromethane or dichloroethane; an ether such as diethyl ether, butyl ethyl ether, methyl tert-butyl ether or dimethoxyethane; a polar aprotic solvent such as acetonitrile, propionitrile, N,N-dimethylformamide, dimethylsulfoxide, sulfolane, N,N-dimethylacetamide, N-methylpyrrolidone or 1,3-dimethyl-2-imidazolidinone; an ester such as methyl acetate, ethyl acetate or propyl acetate; a ketone such as acetone, methyl ethyl ketone or methyl isobutyl ketone; a heterocyclic compound such as tetrahydrofuran, dioxane, pyridine or thiophene; or water. Among them, preferred is an alcohol, an aromatic hydrocarbon, an ether, a ketone, water or the like. The above solvents may be used alone or in combination of two or more.

The solvent may be used in an amount of usually from 0.1 to 10 times, preferably from 0.5 to 5 times the volume of the compound of the formula (II). However, depending upon the reaction conditions, an amount out of such a range may be used.

In the reaction [A], the reaction temperature of the first step is usually from 0 to 200° C., preferably from 50 to 150° C., and the reaction time is usually from 1 to 30 hours.

In the reaction [A], in the second step, hydrolysis is carried out usually in the presence of a base, followed by acidification with an acid to obtain a compound of the formula (I).

The base may, for example, be an alkali metal hydride such as sodium hydride or potassium hydride; an alkali metal hydroxide such as sodium hydroxide, potassium hydroxide or lithium hydroxide; an alkaline earth metal hydroxide such as calcium hydroxide or magnesium hydroxide; an alkali metal such as sodium or potassium; an alkali metal alkoxide such as sodium methoxide, sodium ethoxide or potassium tert-butoxide; an alkali metal carbonate such as sodium carbonate or potassium carbonate; an alkaline earth metal bicarbonate such as calcium bicarbonate or magnesium bicarbonate; an alkali metal bicarbonate such as sodium bicarbonate or potassium bicarbonate; an alkali metal carboxylate such as sodium acetate or potassium acetate; an alkaline earth metal carboxylate such as calcium acetate or magnesium acetate; or a tertiary amine such as trimethylamine, triethylamine, diisopropylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene or 1,4-diazabicyclo[2.2.2]octane. Among them, preferred is an alkali metal hydroxide, an alkaline earth metal hydroxide, an alkali metal carbonate, an alkali metal bicarbonate or the like. Further, among them, preferred is an alkali metal hydroxide in view of shortening of the reaction time, the production cost, etc. The alkali metal hydroxide is preferably sodium hydroxide or potassium hydroxide. The above bases may be used alone or in combination of two or more.

The base may be used in an amount of usually from 1 to 10 equivalent amount, preferably from 1 to 3 equivalent amount per 1 mol of the compound of the formula (II). However, depending upon the reaction conditions, an amount out of such a range may be used.

The acid used for acidification may, for example, be an inorganic acid such as hydrochloric acid, sulfuric acid, phosphoric acid or nitric acid, and is preferably hydrochloric acid, sulfuric acid or the like.

The amount of the acid used may properly be set so long as the pH in the reaction system becomes at most 1.5. For example, the acid may be used in an amount of usually from 1 to 15 equivalent amount, preferably from 1 to 6 equivalent amount per 1 mol of the compound of the formula (II). However, depending upon the reaction conditions, an amount out of such a range may be used.

In the reaction [A], the second step may be carried out in the presence of a solvent as a case requires.

The solvent is not particularly limited so long as it is inert to the reaction and may, for example, be an alcohol such methanol, ethanol, propanol, n-butanol or tert-butanol; an aliphatic hydrocarbon such as pentane, hexane, heptane, octane or cyclohexane; an aromatic hydrocarbon such as benzene, toluene or xylene; a halogenated hydrocarbon such as chlorobenzene, dichlorobenzene, dichloromethane or dichloroethane; an ether such as diethyl ether, butyl ethyl ether, methyl tert-butyl ether or dimethoxyethane; a polar aprotic solvent such as acetonitrile, propionitrile, N,N-dimethylformamide, dimethylsulfoxide, sulfolane, N,N-dimethylacetamide, N-methylpyrrolidone or 1,3-dimethyl-2-imidazolidinone; a ketone such as acetone, methyl ethyl ketone or methyl isobutyl ketone; a heterocyclic compound such as tetrahydrofuran, dioxane, pyridine or thiophene; or water. Among them, preferred is an alcohol, an aromatic hydrocarbon, an ether, a ketone, water or the like. The above solvents may be used alone or in combination of two or more.

The solvent may be used in an amount of usually from 0.1 to 10 times, preferably from 2 to 8 times the volume of the compound of the formula (II). However, depending upon the reaction conditions, an amount out of such a range may be used.

In the reaction [A], the reaction temperature of the hydrolysis step in the second step is usually from 0 to 150° C., preferably from 20 to 100° C., and the reaction time is usually from 0.1 to 10 hours. Further, the reaction temperature of the acidification step in the second step is usually from −20 to 100° C., preferably from 0 to 50° C., and the reaction time is usually from 0.1 to 5 hours.

The first step and the second step in the reaction [A] may be carried out continuously without isolating or purifying the compound of the formula (III).

The compound of the above formula (II) includes a novel compound, and it can be produced by the reaction [B] or [C].

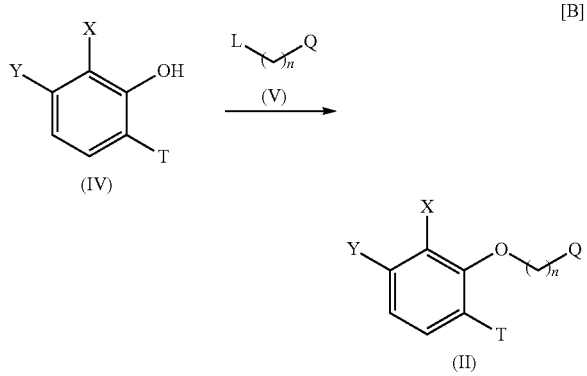

In the above formula, Q, T, X, Y and n are as defined above.

L is a chlorine atom, a bromine atom or an iodine atom, and is preferably a chlorine atom or a bromine atom.

In the reaction [B], the compound of the formula (V) is used usually in an amount of from 1 to 5 equivalent amount, preferably from 1 to 1.5 equivalent amount per 1 mol of the compound of the formula (IV). However, depending upon the reaction conditions, an amount out of such a range may be used.

The reaction [B] may be carried out usually in the presence of a base and a solvent.

The base may, for example, be the same base as mentioned in the second step of the above reaction [A]. Among them, preferred is an alkali metal hydride, an alkali metal hydroxide, an alkali metal carbonate, an alkaline earth metal bicarbonate, triethylamine or the like. Further, among them, preferred is an alkali metal carbonate or triethylamine with a view to further improving the yield. The alkali metal carbonate is preferably sodium carbonate or potassium carbonate. The above bases may be used alone or in combination of two or more.

The base may be used usually in an amount of from 1 to 10 equivalent amount, preferably from 1 to 3 equivalent amount per 1 mol of the compound of the formula (IV). However, depending upon the reaction conditions, an amount out of such a range may be used.

The solvent is not particularly limited so long as it is inert to the reaction and may, for example, be an alcohol such as methanol, ethanol, propanol, n-butanol or tert-butanol; an aliphatic hydrocarbon such as pentane, hexane, heptane, octane or cyclohexane; an aromatic hydrocarbon such as benzene, toluene or xylene; a halogenated hydrocarbon such as chlorobenzene, dichlorobenzene, dichloromethane or dichloroethane; an ether such as diethyl ether, butyl ethyl ether, methyl tert-butyl ether, tetrahydrofuran, dioxane or dimethoxyethane; a polar aprotic solvent such as acetonitrile, propionitrile, N,N-dimethylformamide, dimethylsulfoxide, sulfolane, N,N-dimethylacetamide or N-methylpyrrolidone; an ester such as methyl acetate, ethyl acetate or propyl acetate; or a ketone such as acetone, methyl ethyl ketone or methyl isobutyl ketone. Among them, preferred is an aromatic hydrocarbon, an ether, a polar aprotic solvent, a ketone or the like. The above solvents may be used alone or in combination or two or more.

The solvent may be used in an amount of usually from 0.1 to 10 times the volume of the compound of the formula (IV). However, depending upon the reaction conditions, an amount out of such a range may be used.

The reaction [B] may be carried out in the presence of various additives as the case requires. The reaction will be accelerated by being carried out in the presence of additives.

Such additives may, for example, be an alkali metal halide such as potassium iodide, sodium iodide or potassium bromide; a quaternary ammonium compound such as tetrabutylammonium bromide, tetraethylammonium iodide or tetramethylammonium hydroxide; or a crown ether such as 18-crown-6, 15-crown-5 or dibenzo-18-crown-6. The above additives may be used alone or in combination or two or more.

When such additives are used, they may be used in an amount of usually from 0.001 to 0.5 equivalent amount, preferably from 0.01 to 0.2 equivalent amount per 1 mol of the compound of the formula (IV). However, depending upon the reaction conditions, an amount out of such a range may be used.

The reaction temperature of the reaction [B] is usually from 0 to 200° C., preferably from 50 to 150° C., and the reaction time is usually from 1 to 30 hours.

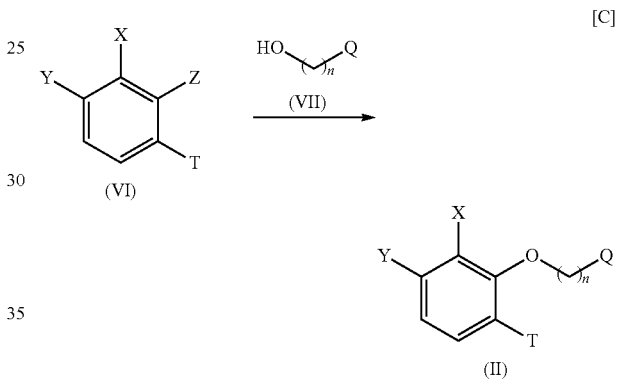

In the above formula, Q, T, X, Y and n are as defined above.

Z is a chlorine atom, a bromine atom or an iodine atom, and is preferably a chlorine atom or a bromine atom.

In the reaction [C], the compound of the formula (VII) may be used in an amount of usually from 1 to 5 equivalent amount, preferably from 1 to 1.5 equivalent amount per 1 mol of the compound of the formula (VI). However, depending upon the reaction conditions, an amount out of such a range may be used.

The reaction [C] may be carried out usually in the presence of a base and a solvent.

The base may, for example, be the same base as mentioned in the second step in the above reaction [A]. Among them, preferred is an alkali metal hydride, an alkali metal hydroxide, an alkaline earth metal hydroxide, an alkali metal, an alkali metal carbonate, triethylamine or the like. Further, among them, preferred is an alkali metal hydride, an alkali metal hydroxide or an alkali metal with a view to further improving the yield. The alkali metal hydride is preferably sodium hydride or potassium hydride, the alkali metal hydroxide is preferably sodium hydroxide, potassium hydroxide or lithium hydroxide, and the alkali metal is preferably sodium. The above bases may be used alone or in combination of two or more.

The base may be used in an amount of usually from 1 to 10 equivalent amount, preferably from 1 to 3 equivalent amount per 1 mol of the compound of the formula (VI).

However, depending upon the reaction conditions, an amount out of such a range may be used.

The solvent is not particularly limited so long as it is inert to the reaction and may, for example, be the same solvent as mentioned in the above reaction [B]. Among them, preferred is an aromatic hydrocarbon, an ether, a polar aprotic solvent, a heterocyclic compound or the like. The above solvents may be used alone or in combination of two or more.

The solvent may be used in an amount of usually from 0.1 to 10 times the volume of the compound of the formula (VI). However, depending upon the reaction conditions, an amount out of such a range may be used.

The reaction temperature of the reaction [C] is usually from 0 to 200° C., preferably from 50 to 150° C., and the reaction time is usually from 1 to 30 hours.

The compound of the above formula (IV) includes a novel compound, and it can be produced by the reaction [D] or [E].

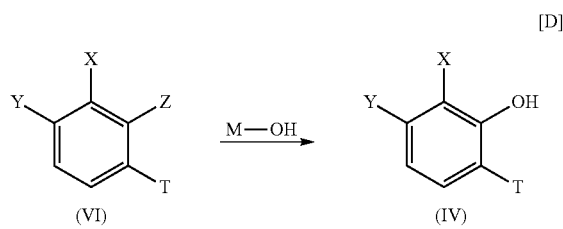

[D]

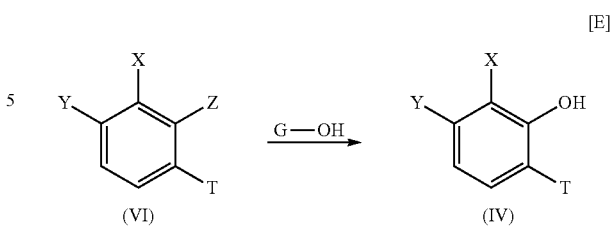

[E]

In the above formula, T, X, Y and Z are as defined above.

M is lithium, sodium or potassium, preferably sodium or potassium.

In the reaction [D], the compound represented by the formula M-OH may be used in an amount of usually from 1 to 20 equivalent amount, preferably from 1 to 10 equivalent amount per 1 mol of the compound of the formula (VI). However, depending upon the reaction conditions, an amount out of such a range may be used.

The reaction [D] may be carried out usually in the presence of a solvent, and by acidification with an acid, the compound of the formula (IV) can be obtained.

The solvent is not particularly limited so long as it is inert to the reaction and may, for example, be the same solvent as mentioned in the first step of the above reaction [A]. Among them, preferred is an alcohol, an aromatic hydrocarbon, a polar aprotic solvent, a heterocyclic compound, water, chlorobenzene, dichlorobenzene or the like. The above solvents may be used alone or in combination of two or more.

The solvent may be used in an amount of usually from 0.1 to 10 times, preferably from 2 to 6 times the volume of the compound of the formula (VI). However, depending upon the reaction conditions, an amount out of such a range may be used.

The acid used for acidification may, for example, be the same acid as mentioned in the second step of the above reaction [A].

The reaction temperature of the reaction [D] is usually from 0 to 200° C., preferably from 50 to 150° C., and the reaction time is usually from 1 to 40 hours.

In the above formula, T, X, Y and Z are as defined above.

G is a hydrogen atom or alkyl, preferably alkyl. The alkyl is one having from 1 to 6 carbon atoms, and may be either linear or branched.

In the reaction [E], the compound represented by the formula G-OH may be used in an amount of usually from 1 to 20 equivalent amount, preferably from 1 to 5 equivalent amount per 1 mol of the compound of the formula (VI). Further, if it is used in an excessive amount, it also functions as a solvent. However, depending upon the reaction conditions, an amount out of such a range may be used.

The reaction [E] may be carried out usually in the presence of a base and a solvent, and by acidification with an acid, the compound of the formula (IV) can be obtained.

The base may, for example, be the same base as mentioned in the second step in the above reaction [A]. Among them, preferred is an alkali metal hydride, an alkali metal hydroxide, an alkali metal alkoxide or the like. Further, among them, preferred is an alkali metal hydride or an alkali metal hydroxide, with a view to further improving the yield. The alkali metal hydride is preferably sodium hydride or potassium hydride, and the alkali metal hydroxide is preferably sodium hydroxide, potassium hydroxide or lithium hydroxide. The above bases may be used alone or in combination of two or more.

The base may be used in an amount of usually from 1 to 10 equivalent amount, preferably from 1 to 5 equivalent amount per 1 mol of the compound of the formula (VI). However, depending upon the reaction conditions, an amount out of such a range may be used.

The solvent is not particularly limited so long as it is inert to the reaction and may, for example, be the same solvent as mentioned in the first step of the above reaction [A]. Among them, preferred is an alcohol, an aromatic hydrocarbon, a polar aprotic solvent, a heterocyclic compound, water or the like. The above solvents may be used alone or in combination of two or more.

The solvent may be used in an amount of usually from 0.1 to 10 times, preferably from 2 to 6 times the volume of the compound of the formula (VI). However, depending upon the reaction conditions, an amount out of such a range may be used.

The acid used for acidification may, for example, be the same acid as mentioned in the second step of the above reaction [A].

The reaction temperature of the reaction [E] is usually from 0 to 200° C., preferably from 50 to 150° C., and the reaction time is usually from 1 to 40 hours.

Now, preferred embodiments of the present invention will be described, however, it should be understood that the present invention is by no means restricted thereto.

(1) A method for producing the compound of the above formula (I), wherein in the reaction [A], Q is dioxolan-2-yl, T is methylsulfonyl, X is a chlorine atom, Y is a bromine atom and n is 2.

(2) A method for producing the compound of the above formula (II), wherein in the reaction [B], Q is dioxolan-2-yl, T is methylsulfonyl, X is a chlorine atom, Y is a bromine atom, n is 2 and L is a bromine atom.

(3) A method for producing the compound of the above formula (II), wherein in the reaction [C], Q is dioxolan-2-yl, T is methylsulfonyl, X is a chlorine atom, Y is a bromine atom, n is 2 and Z is a chlorine atom.

(4) A method for producing the compound of the above formula (IV), wherein in the reaction [D], T is methylsulfonyl, X is a chlorine atom, Y is a bromine atom and Z is a chlorine atom.

(5) A method for producing the compound of the above formula (IV), wherein in the reaction [E], T is methylsulfonyl, X is a chlorine atom, Y is a bromine atom and Z is a chlorine atom.

(6) The compound of the above formula (II), wherein Q is dioxolan-2-yl, T is methylsulfonyl, X is a chlorine atom, Y is a bromine atom and n is 2.

(7) The compound of the above formula (IV), wherein T is methylsulfonyl, X is a chlorine atom and Y is a bromine atom.

Using the compound of the above formula (I) produced by the present invention, in accordance with JP-A-2006-16389, compounds as identified in Table 1 may, for example, be produced.

Physical properties (melting point and $^1$H-NMR measurement values) of such compounds are as identified in Tables 2 and 3.

These compounds are useful compounds having herbicidal activity.

In Table 1, Ph represents a phenyl group.

TABLE 1

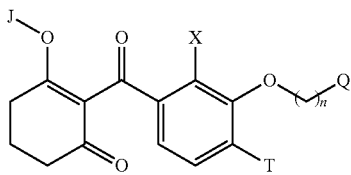

| Compound No. | X | T | J | n | Q |
|---|---|---|---|---|---|
| 1 | Cl | SO$_2$CH$_3$ | H | 1 | (1,3-dioxolan-4-yl) |
| 2 | Cl | SO$_2$CH$_3$ | H | 1 | (1,3-dioxan-4-yl) |
| 3 | Cl | SO$_2$CH$_3$ | H | 1 | (2-methyl-1,3-dioxan-4-yl) |
| 4 | Cl | SO$_2$CH$_3$ | H | 2 | (1,3-dioxolan-2-yl) |
| 5 | Cl | SO$_2$CH$_3$ | Na | 2 | (1,3-dioxolan-2-yl) |

TABLE 1-continued

| Compound No. | X | T | J | n | Q |
|---|---|---|---|---|---|
| 6 | Cl | SO$_2$CH$_3$ | H | 2 | (1,3-dioxolan-4-yl) |
| 7 | Cl | SO$_2$CH$_3$ | H | 2 | (2-methyl-1,3-dioxolan-4-yl) |
| 8 | Cl | SO$_2$CH$_3$ | H | 2 | (1,3-dioxan-4-yl) |
| 9 | Cl | SO$_2$CH$_3$ | H | 2 | (1,3-dioxan-2-yl) |
| 10 | Cl | SO$_2$CH$_3$ | H | 2 | (2,6-dimethyl-1,3-dioxan-4-yl) |
| 11 | Cl | SO$_2$CH$_3$ | H | 2 | (2,5,5-trimethyl-1,3-dioxan-4-yl) |
| 12 | Cl | SO$_2$CH$_3$ | H | 2 | CH(OCH$_2$CH$_3$)$_2$ |

TABLE 2

| Compound No | Melting point |
|---|---|
| 1 | 115 to 118° C. |
| 6 | 125 to 127° C. |

TABLE 3

| Compound No | $^1$H-NMR(①CDCl$_3$, 300 MHz or ②DMSO-d6, 400 MHz): δ(ppm) |
|---|---|
| 2 | ①: 1.54-1.58(m, 1H), 1.91-2.0(m, 1H), 2.09(t, 2H), 2.45(t, 2H), 2.82(t, 2H), 3.32(s, 3H), 3.81(dt, 1H), 4.15-4.45(m, 3H), 4.80(d, 1H), 5.16(d, 1H), 7.10(d, 1H), 7.95(d, 1H) |
| 3 | ①: 1.36(d, 3H), 1.52-1.49(m, 1H), 1.80-1.92(m, 1H), 2.07(t, 2H), 2.44(t, 2H), 2.81(t, 2H), 3.13(s, 3H), 3.83(dt, 1H), 4.19-4.14(m, 3H), 4.40(q, 1H), 4.79(q, 1H), 7.08(d, 1H), 7.94(d, 1H) |
| 4 | ①: 2.0(t, 2H), 2.18-2.24(m, 2H), 2.38(t, 2H), 2.74(t, 2H), 3.22(s, 3H), 3.80-3.83(m, 2H), 3.91-3.94(m, 2H), 4.32(t, 2H), 5.08(t, 1H), 6.99(d, 1H), 7.85(d, 1H) |

TABLE 3-continued

| Compound No | $^1$H-NMR(①CDCl$_3$, 300 MHz or ②DMSO-d6, 400 MHz): δ(ppm) |
|---|---|
| 5 | ②: 1.75(m, 2H), 2.14(m, 2H), 2.49(m, 4H), 3.30(s, 3H), 3.78(t, 2H), 3.90(t, 2H), 4.19(t, 2H), 5.02(t, 1H), 6.87(d, 1H), 7.60(d, 1H) |
| 7 | ①: 1.26-1.30(m, 3H), 2.07(t, 2H), 2.24-2.29(m, 2H), 2.44(t, 2H), 2.81(t, 2H), 3.29(s, 3H), 3.40-3.47(m, 1H), 3.96(m, 1H), 4.15-4.17(m, 1H), 4.27-4.40(m, 2H), 5.18(t, 1H), 7.06(d, 1H), 7.92(d, 1H) |
| 8 | ①: 1.57-1.62(m, 1H), 1.83-1.89(m, 1H), 2.03-2.14(m, 4H), 2.45(t, 2H), 2.82(t, 2H), 3.25(s, 3H), 3.74(dt, 1H), 3.89-3.93(m, 1H), 4.10-4.15(m, 1H), 4.33-4.39(m, 2H), 4.72(d, 1H), 5.05(d, 1H), 7.06(d, 1H), 7.92(d, 1H) |
| 9 | ①: 1.33-1.38(m, 1H), 2.05-2.22(m, 5H), 2.45(t, 2H), 2.82(t, 2H), 3.27(s, 3H), 3.79(dt, 2H), 4.09-4.14(m, 2H), 4.35(t, 2H), 4.85(t, 1H), 7.05(d, 1H), 7.92(d, 1H) |
| 10 | ①: 1.24(d, 6H), 1.53-1.60(m, 2H), 2.07(t, 2H), 2.24(q, 2H), 2.48(t, 2H), 2.80(t, 2H), 3.26(s, 3H), 3.75(m, 2H), 4.39(t, 2H), 4.89(t, 1H), 7.05(d, 1H), 7.90(d, 1H) |
| 11 | ①: 0.72(s, 3H), 1.20(s, 3H), 2.05(t, 2H), 2.22(q, 2H), 2.44(t, 2H), 2.80(t, 2H), 3.28(s, 3H), 3.46(d, 2H), 3.63(d, 2H), 4.38(t, 2H), 4.76(t, 1H), 7.08(d, 1H), 7.94(d, 1H) |
| 12 | ①: 1.24(t, 6H), 2.08(t, 2H), 2.22(q, 2H), 2.45(t, 2H), 2.82(t, 2H), 3.26(s, 3H), 3.56(q, 2H), 3.71(q, 4H), 4.33(t, 2H), 4.83(t, 1H), 7.06(d, 1H), 7.93(d, 1H) |
| 13 | ①: 2.05(t, 2H), 2.20-2.26(m, 2H), 2.45(t, 2H), 2.80(t, 2H), 3.25(s, 3H), 3.82-3.85(m, 2H), 3.93-3.96(m, 2H), 4.32(t, 2H), 5.08(t, 1H), 7.37-7.65(m, 6H), 7.85(d, 1H) |

EXAMPLES

Now, the present invention will be described in further detail with reference to Examples (Preparation Examples). However, it should be understood that the present invention is by no means restricted to such specific Examples.

Preparation Example 1

(1) 448.9 g (1.41 mol) of 1-bromo-2,3-dichloro-4-(methylsulfonyl)benzene, 1716 mL of toluene, 42.9 mL of N-methylpyrrolidone and 282 g of sodium hydroxide were mixed and reacted under reflux for 7 hours. 2571 mL of water was put into the reaction liquid at from 40 to 50° C. to completely dissolve 3-bromo-2-chloro-6-(methylsulfonyl)phenol sodium salt. Then, toluene was removed by liquid separation to obtain an aqueous solution of 3-bromo-2-chloro-6-(methylsulfonyl)phenol sodium salt. The obtained sodium salt aqueous solution was acidified with 40 mass % sulfuric acid (760 g) to precipitate crystals. The precipitated crystals were collected by filtration, washed with water and dried to obtain 401.4 g (purity: 95.2%, yield: 94.9%) of 3-bromo-2-chloro-6-(methylsulfonyl)phenol having a melting point of from 157 to 160° C. $^1$H-NMR spectrum data of this compound are as follows.

$^1$H NMR (500 MHz, CDCl$_3$) δ:9.04 (s, 1H), 7.54 (d, J=8.5 Hz, 1H), 7.38 (d, J=8.5 Hz, 1H), 3.16 (s, 3H)

(2) 176.7 g of potassium carbonate and 300 mL of N,N'-dimethylformamide were mixed, and with stirring, 300 g (0.985 mol, purity: 93.7%) of 3-bromo-2-chloro-6-(methylsulfonyl)phenol was put and then 257 g (purity: 90%) of 2-(2-bromoethyl)-1,3-dioxolane was put, followed by reaction at 100° C. for 3 hours. After the reaction, the reaction liquid was cooled to 20° C., 1200 mL of toluene and 1200 mL of water were added for extraction, followed by liquid separation. The resulting organic layer was washed with 600 mL of a 5 mass % sodium hydroxide aqueous solution, followed by liquid separation. The obtained organic liquid was concentrated under reduced pressure to obtain 700 g (purity: 48.7%, yield: 89.7%) of a 2-(2-(3-bromo-2-chloro-6-(methylsulfonyl)phenoxy)ethyl)-1,3-dioxolane toluene solution.

(3) 225 g (purity: 40.3%, 0.23 mol) of the 2-(2-(3-bromo-2-chloro-6-(methylsulfonyl)phenoxy)ethyl)-1,3-dioxolane toluene solution, 106.1 g of methanol, 41.9 g of potassium carbonate, 45 g of water, 1.8 g (50% wet) of 5%-palladium on carbon and 0.45 g of 1,4-bis(diphenylphosphino)butane were charged into a 900 mL autoclave, and the atmosphere in the reactor was replaced twice with a carbon monoxide gas. After replacement, 2.0 MPa of a carbon monoxide gas was introduced, followed by reaction at 100° C. for 4 hours. The reaction liquid was cooled to 20° C., and then the pressure in the reactor was recovered to normal pressure, and 90 g of water and 117 g of toluene were added to dilute the reaction liquid. The palladium on carbon was removed by filtration with celite, and 90 g of water and 39 g of toluene were poured for washing, to obtain a toluene-water mixed liquid of methyl 3-(2-(1,3-dioxolan-2-yl)ethoxy)-2-chloro-4-(methylsulfonyl)benzoate.

13.6 g of sodium hydroxide was put into the obtained mixed liquid, followed by reaction at 50° C. for one hour. After completion of the reaction, the toluene layer was removed by liquid separation to obtain a sodium 3-(2-(1,3-dioxolan-2-yl)ethoxy)-2-chloro-4-(methylsulfonyl)benzoate aqueous solution.

The obtained aqueous solution was acidified with concentrated hydrochloric acid at from 5 to 10° C. to precipitate crystals. The precipitated crystals were collected by filtration, washed with water and dried under reduced pressure to obtain 81 g (purity: 89.9%, yield: 89.3%) of 3-(2-(1,3-dioxolan-2-yl)ethoxy)-2-chloro-4-(methylsulfonyl)benzoic acid having a melting point of from 142 to 144° C. $^1$H-NMR spectrum data of this compound are as follows.

$^1$H NMR (500 MHz, CDCl$_3$) δ:7.97 (d, J=8.5 Hz, 1H), 7.82 (d, J=8.5 Hz, 1H), 5.18 (t, J=4.5 Hz, 1H), 4.43 (t, J=6.5 Hz, 2H), 4.03 (m, 2H), 3.91 (m, 2H), 3.31 (s, 3H), 2.33 (m, 2H)

Preparation Example 2

31 g (0.1 mol) of 1-bromo-2,3-dichloro-4-(methylsulfonyl)benzene, 121 mL of toluene, 3 mL of dimethylsulfoxide and 20.3 g of sodium hydroxide were mixed and reacted under reflux for 5 hours. After the reaction, 225 mL of water was put into the reaction liquid to completely dissolve 3-bromo-2-chloro-6-(methylsulfonyl)phenol sodium salt, and then toluene was removed by liquid separation to obtain an aqueous solution of 3-bromo-2-chloro-6-(methylsulfonyl)phenol sodium salt. The obtained aqueous solution of sodium salt was acidified with concentrated hydrochloric acid to a pH of at most 1 to precipitate crystals. The precipitated crystals were collected by filtration, washed with water and dried to obtain 27.97 g (purity: 90.75%, yield: 90.08%) of 3-bromo-2-chloro-6-(methylsulfonyl)phenol.

Preparation Example 3

The same operation as in Preparation Example 2 was carried out except that 3 mL of 1,3-dimethyl-2-imidazolidinone was used instead of dimethylsulfoxide. The reaction was completed in 11 hours, and 28.13 g (purity: 92.95%, yield: 92.8%) of 3-bromo-2-chloro-6-(methylsulfonyl)phenol was obtained.

Preparation Example 4

The same operation as in Preparation Example 2 was carried out except that 151 mL of tert-butyl alcohol was used instead of toluene and dimethylsulfoxide, and the amount of sodium hydroxide used was 16.3 g. The reaction was completed in 9 hours, and 29.73 g (purity: 91.84%, yield: 95.6%) of 3-bromo-2-chloro-6-(methylsulfonyl)phenol was obtained.

Preparation Example 5

51 g (0.16 mol) of 1-bromo-2,3-dichloro-4-(methylsulfonyl)benzene, 150 mL of pyridine and 14.9 g of sodium hydroxide were mixed and reacted under reflux for 7 hours. 357 mL of water was put into the reaction liquid to completely dissolve 3-bromo-2-chloro-6-(methylsulfonyl)phenol sodium salt, followed by acidification with concentrated hydrochloric acid to a pH of at most 1 to precipitate crystals. The precipitated crystals were collected by filtration, washed with water and dried to obtain 42.56 g (purity: 94.46%, yield: 85.6%) of 3-bromo-2-chloro-6-(methylsulfonyl)phenol.

Preparation Example 6

5.8 g (0.016 mol) of 1-bromo-2,3-dichloro-4-(methylsulfonyl)benzene, 15 mL of tert-butyl alcohol and 2.7 g of potassium hydroxide were mixed and reacted under reflux for 7 hours. 34.2 mL of water was put into the reaction liquid to completely dissolve 3-bromo-2-chloro-6-(methylsulfonyl)phenol potassium salt, followed by acidification with concentrated hydrochloric acid to a pH of at most 1 to precipitate crystals. The precipitated crystals were collected by filtration, washed with water and dried to obtain 4.99 g (purity: 73.6%, yield: 77.6%) of 3-bromo-2-chloro-6-(methylsulfonyl)phenol.

Preparation Example 7

The same operation as in Preparation Example 6 was carried out except that 4.7 g of potassium tert-butoxide was used instead of potassium hydroxide. The reaction was completed in one hour, and 4.84 g (purity: 63.28%, yield: 64.76%) of 3-bromo-2-chloro-6-(methylsulfonyl)phenol was obtained.

Preparation Example 8

25 mL of tert-butyl alcohol and 1.7 g of sodium hydride (60% oil suspension) were mixed and reacted at 70° C. for one hour, and then 5.8 g (0.016 mol) of 1-bromo-2,3-dichloro-4-(methylsulfonyl)benzene was put, followed by reaction under reflux for 20 hours. 50 mL of water was put into the reaction liquid to completely dissolve 3-bromo-2-chloro-6-(methylsulfonyl)phenol sodium salt, followed by acidification with concentrated hydrochloric acid to a pH of at most 1 to precipitate crystals. The precipitated crystals were collected by filtration, washed with water and dried to obtain 5.63 g (purity: 76.22%, yield: 90.7%) of 3-bromo-2-chloro-6-(methylsulfonyl)phenol.

Preparation Example 9

12.6 g of potassium carbonate and 20 mL of N,N'-dimethylformamide were mixed, and with stirring, 21 g (0.07 mol, purity: 91.5%) of 3-bromo-2-chloro-6-(methylsulfonyl)phenol was put, and then 17 g (purity: 96%) of 2-(2-bromoethyl)-1,3-dioxolane was put, followed by reaction at from 85 to 105° C. for 6 hours. After the reaction, the reaction liquid was cooled to 20° C., 60 mL of water was added, and seed crystals were added with stirring to precipitate crystals. The precipitated crystals were collected by filtration, washed with water and dried to obtain 29.2 g (purity: 88.9%, yield: 96.0%) of 2-(2-(3-bromo-2-chloro-6-(methylsulfonyl)phenoxy)ethyl)-1,3-dioxolane having a melting point of from 74 to 75° C. $^1$H-NMR spectrum data of this compound are as follows.

$^1$H NMR (500 MHz, CDCl$_3$) δ:7.75 (d, J=8.5 Hz, 1H), 7.60 (d, J=8.5 Hz, 1H), 5.16 (t, J=4.5 Hz, 1H), 4.39 (t, J=6.0 Hz, 2H), 4.01 (m, 2H), 3.89 (m, 2H), 3.26 (s, 3H), 2.30 (m, 2H)

Preparation Example 10

50 g (0.159 mol, purity: 90.9%) of 3-bromo-2-chloro-6-(methylsulfonyl)phenol, 25 mL of toluene and 20.9 g of triethylamine were mixed and heated to 100° C. Then, 41.6 g (purity: 90%) of 2-(2-bromoethyl)-1,3-dioxolane was put, followed by reaction at 100° C. for 3 hours. After the reaction, the reaction liquid was cooled to 20° C., and 175 mL of toluene and 200 mL of water were added for extraction, followed by liquid separation. The resulting organic layer was washed with 200 mL of a 5 mass % sodium hydroxide aqueous solution, followed by liquid separation. The obtained organic layer was concentrated under reduced pressure to obtain 101.8 g (purity: 54.2%, yield: 89.9%) of a 2-(2-(3-bromo-2-chloro-6-(methylsulfonyl)phenoxy)ethyl)-1,3-dioxolane toluene solution.

Preparation Example 11

17.9 g of potassium carbonate and 29 mL of N-methylpyrrolidone were mixed, and with stirring, 31.5 g (0.1 mol, purity: 90.7%) of 3-bromo-2-chloro-6-(methylsulfonyl)phenol was put, and then 18.5 g (purity: 96%) of 2-(2-chloroethyl)-1,3-dioxolane and 1.66 g of potassium iodide were put, followed by reaction at 120° C. for 5 hours. After the reaction, the reaction liquid was cooled to 20° C., and 103 mL of toluene and 103 mL of water were added for extraction, followed by liquid separation. The organic layer was washed with a 5 mass % sodium hydroxide aqueous solution, followed by liquid separation. The obtained organic layer was concentrated under reduced pressure to obtain 95.3 g (purity: 39.4%, yield: 97.4%) of a 2-(2-(3-bromo-2-chloro-6-(methylsulfonyl)phenoxy)ethyl)-1,3-dioxolane toluene solution.

Preparation Example 12

17.9 g of potassium carbonate and 29 mL of N-methylpyrrolidone were mixed, and with stirring, 31.5 g (0.1 mol, purity: 90.7%) of 3-bromo-2-chloro-6-(methylsulfonyl)phenol was put and then, 18.5 g (purity: 96%) of 2-(2-chloroethyl)-1,3-dioxolane was put, followed by reaction at 120° C. for 23 hours. After the reaction, the reaction liquid was cooled to 20° C., and 103 mL of toluene and 103 mL of water were added for extraction, followed by liquid separation. The organic layer was washed with a 5 mass % sodium hydroxide aqueous solution, followed by liquid separation. The obtained organic layer was concentrated under reduced pressure to obtain 95.0 g (purity: 37.5%, yield: 92.5%) of a 2-(2-(3-bromo-2-chloro-6-(methylsulfonyl)phenoxy)ethyl)-1,3-dioxolane toluene solution.

Preparation Example 13

46.7 g (purity: 42.8%, 0.05 mol) of a 2-(2-(3-bromo-2-chloro-6-(methylsulfonyl)phenoxy)ethyl)-1,3-dioxolane toluene solution, 23.5 g of methanol, 13.6 g of triethylamine, 10 g of water, 0.4 g (50% wet) of 5%-palladium on carbon and 0.1 g of 1,4-bis(diphenylphosphino)butane were charged in a 200 mL autoclave, and the atmosphere in the reactor was replaced twice with a carbon monoxide gas. After replacement, 2.0 MPa of a carbon monoxide gas was introduced, followed by reaction at 120° C. for 5 hours. Then, the reaction liquid was cooled to 20° C., the pressure in the reactor was recovered to normal pressure, and 40 g of water and 40 mL of toluene were added to dilute the reaction liquid. Then, the palladium on carbon was removed by filtration with celite, to obtain a toluene-water mixed liquid of methyl 3-(2-(1,3-dioxolan-2-yl)ethoxy)-2-chloro-4-(methylsulfonyl)benzoate.

3 g of sodium hydroxide was put into the obtained mixed liquid, followed by reaction at 50° C. for one hour. After completion of the reaction, the toluene layer was removed by liquid separation to obtain a sodium 3-(2-(1,3-dioxolan-2-yl)ethoxy)-2-chloro-4-(methylsulfonyl)benzoate aqueous solution.

The obtained aqueous solution was acidified with concentrated hydrochloric acid at from 5 to 10° C. to precipitate crystals. The precipitated crystals were collected by filtration, washed with water and dried under reduced pressure to obtain 16.4 g (purity: 84.8%, yield: 76.7%) of 3-(2-(1,3-dioxolan-2-yl)ethoxy)-2-chloro-4-(methylsulfonyl)benzoic acid.

Preparation Example 14

21.5 g (0.052 mol) of 2-(2-(3-bromo-2-chloro-6-(methylsulfonyl)phenoxy)ethyl)-1,3-dioxolane, 11 g of triethylamine, 0.4 g (50% wet) of 5%-palladium on carbon, 0.1 g of 1,4-bis(diphenylphosphino)butane and 60 mL of methanol were charged in a 200 mL autoclave, and the atmosphere in the reactor was replaced twice with a carbon monoxide gas. After replacement, 2.0 MPa of a carbon monoxide gas was introduced, followed by reaction at 110° C. for 3 hours. Then, the reaction liquid was cooled to 20° C., the pressure in the reactor was recovered to normal pressure, and 100 mL of water and 200 mL of toluene were added for extraction with toluene. Then, the toluene layer was washed with a 5 mass % sodium hydroxide aqueous solution and water respectively, and dried over magnesium sulfate. Then, the toluene layer was concentrated. The obtained residue was purified by silica gel column chromatography (as an eluent, hexane:ethyl acetate=3:2 (volume ratio) were used) to obtain 14.3 g (purity: 99%, yield: 75.5%) of methyl 3-(2-(1,3-dioxolan-2-yl)ethoxy)-2-chloro-4-(methylsulfonyl)benzoate. $^1$H-NMR spectrum data of this compound are as follows.

$^1$H NMR (500 MHz, CDCl$_3$) δ: 7.92 (d, J=8.5 Hz, 1H), 7.63 (d, J=8.5 Hz, 1H), 5.16 (t, J=4.5 Hz, 1H), 4.40 (t, J=6.5 Hz, 2H), 4.00 (m, 2H), 3.97 (s, 3H), 3.89 (m, 2H), 3.28 (s, 3H), 2.31 (m, 2H)

Preparation Example 15

1 g (2.59 mmol) of 2-(2-(3-bromo-2-chloro-6-(methylsulfonyl)phenoxy)ethyl)-1,3-dioxolane, 58 mg of palladium acetate, 203 mg of triphenylphosphine, 425 mg of sodium acetate, 10 mL of methanol and 10 mL of 1,3-dioxane were charged in a 100 mL autoclave, and the atmosphere in the reactor was replaced twice with a carbon monoxide gas. After replacement, 2.5 MPa of a carbon monoxide gas was introduced, followed by reaction at 150° C. for 19.5 hours. After the reaction, the reaction liquid was cooled to room temperature, the pressure in the reactor was recovered to normal pressure, and 20 mL of a saturated sodium chloride solution was put. The reaction liquid was extracted with ethyl acetate, and the extract was dried over sodium sulfate. Then, the ethyl acetate layer was concentrated. The obtained residue was purified by silica gel column chromatography (as an eluent, hexane:ethyl acetate=7:3 (volume ratio) were used) to obtain 766.5 mg (yield: 81.1%) of methyl 3-(2-(1,3-dioxolan-2-yl)ethoxy)-2-chloro-4-(methylsulfonyl)benzoate.

Preparation Example 16

1.0 g (3.68 mmol) of 1-bromo-2,3-dichloro-4-(methylsulfonyl)benzene, 0.52 g of 2-(1,3-dioxolan-2-yl)ethanol, 0.29 g of sodium hydroxide and 5 mL of toluene were mixed and reacted at 60° C. for 23 hours. After the reaction, 10 mL of water was added to the reaction liquid under cooling with ice, and ethyl acetate was further added for extraction. Then, the extract was dried over sodium sulfate, and the ethyl acetate solution was concentrated. The obtained residue was purified by silica gel column chromatography (as an eluent, hexane:ethyl acetate=75:25 (volume ratio) were used), to obtain 1.058 g (yield: 74.6%) of 2-(2-(3-bromo-2-chloro-6-(methylsulfonyl)phenoxy)ethyl)-1,3-dioxolane.

INDUSTRIAL APPLICABILITY

According to the present invention, it is possible to obtain a substituted benzoic acid compound useful as an intermediate for production of pharmaceutical and agricultural chemicals, with high purity and high yield, and an industrial method for producing a substituted benzoic acid compound can be provided.

The entire disclosure of Japanese Patent Application No. 2012-107065 filed on May 8, 2012 including specification, claims and abstract is incorporated herein by reference in its entirety.

The invention claimed is:
1. A method for producing a compound represented by the following formula (I):

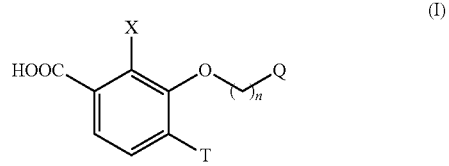

wherein Q is a 5- or 6-membered saturated heterocyclic group, the heterocyclic group can be substituted by alkyl, containing one or two of at least one hetero atom selected from the group consisting of an oxygen atom and a sulfur atom, or Q is dialkoxymethyl;

T is trifluoromethyl, nitro, cyano, —SOA$^1$, —SO$_2$A$^1$, —PO(OA$^1$)(OA$^2$), —COA$^1$, —CO$_2$A$^1$ or —CONA$^1$A$^2$, and each of A$^1$ and A$^2$ which are independent of each other, is a hydrogen atom, alkyl or haloalkyl;

X is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, di(haloalkyl)aminosulfonyl, nitro or cyano; and n is an integer of from 1 to 6;

which comprises reacting a compound represented by the following formula (II):

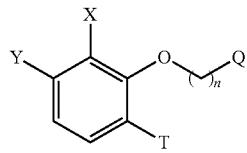

(II)

wherein Y is a chlorine atom, a bromine atom or an iodine atom;

with carbon monoxide and a compound represented by the formula R—OH, wherein R is alkyl, to produce a compound represented by the following formula (III):

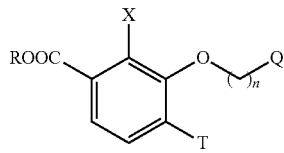

(III)

and hydrolyzing the compound of the formula (III).

2. The production method according to claim 1, wherein the reaction of the compound represented by the above formula (II), carbon monoxide and the compound represented by the formula R—OH is carried out in the presence of a base and a transition metal catalyst, and further as the case requires, in the presence of a solvent.

3. The production method according to claim 1, wherein the hydrolysis is carried out in the presence of a base, and then the reaction mixture is acidified with an acid.

4. A compound represented by the formula (II):

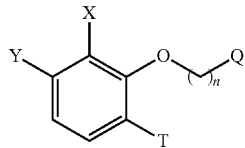

(II)

wherein Q is a 5- or 6-membered saturated heterocyclic group the heterocyclic group can be substituted by alkyl, containing one or two of at least one hetero atom selected from the group consisting of an oxygen atom and a sulfur atom, or Q is dialkoxymethyl;

T is trifluoromethyl, nitro, cyano, —SOA$^1$, —SO$_2$A$^1$, —PO(OA$^1$)(OA$^2$), —COA$^1$, —CO$_2$A$^1$ or —CONA$^1$A$^2$, and each of A$^1$ and A$^2$ which are independent of each other, is a hydrogen atom, alkyl or haloalkyl;

X is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, di(haloalkyl)aminosulfonyl, nitro or cyano; and Y is a chlorine atom, a bromine atom or an iodine atom; and n is an integer of from 1 to 6.

5. The compound according to claim 4, wherein Q is dioxolan-2-yl, T is methylsulfonyl, X is a chlorine atom, Y is a bromine atom, and n is 2.

6. A compound represented by the following formula (IV):

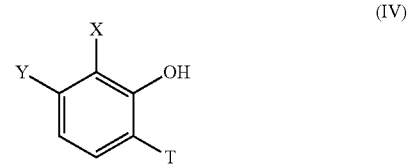

(IV)

wherein T is methylsulfonyl, X is a chlorine atom, and Y is a bromine atom.

7. The production method according to claim 2, wherein the hydrolysis is carried out in the presence of a base, and then the reaction mixture is acidified with an acid.

8. The production method according to claim 1, wherein Q is dioxolan-2-yl, T is methylsulfonyl, X is a chlorine atom, Y is a bromine atom, and n is 2.

* * * * *